United States Patent [19]
Sekine et al.

[11] Patent Number: 5,454,601
[45] Date of Patent: Oct. 3, 1995

[54] PACKING BAG

[75] Inventors: Takayuki Sekine, Saitama; Hiroshi Yamaguchi, Tokyo, both of Japan

[73] Assignee: Alcare Co., Ltd., Japan

[21] Appl. No.: 23,336

[22] Filed: Feb. 26, 1993

[30] Foreign Application Priority Data

Feb. 28, 1992 [JP] Japan ................. 4-018909 U

[51] Int. Cl.$^6$ .............. B65D 30/02; B65D 3/26
[52] U.S. Cl. .............. 383/200; 206/204; 383/109
[58] Field of Search .............. 383/109, 113, 383/200, 208, 209; 206/204

[56] References Cited

U.S. PATENT DOCUMENTS

| | | | |
|---|---|---|---|
| 2,578,324 | 12/1951 | Southwick, Jr. | 206/204 |
| 2,956,723 | 10/1960 | Tritsch | 383/200 |
| 3,084,984 | 4/1963 | Adler | 206/204 |
| 3,272,424 | 9/1966 | Rodkey | 383/208 |
| 4,801,042 | 1/1989 | Homada et al. | 206/204 |
| 4,927,010 | 5/1990 | Kannankeril | 206/204 |

FOREIGN PATENT DOCUMENTS

| | | | |
|---|---|---|---|
| 0715997 | 9/1954 | United Kingdom | 383/113 |

OTHER PUBLICATIONS

Japanese Industrial Standard, JIS K 6772 1976, Japanese Standards Association.

*Primary Examiner*—Stephen P. Garbe
*Attorney, Agent, or Firm*—Haverstock, Garrett & Roberts

[57] ABSTRACT

According to the present invention, a water absorbing member is provided on a portion of the outer surface of a packing bag adjacent at least one sealed peripheral or circumferential side portion of the bag. By grasping this water absorbing portion when ripping or tearing open the bag, it is ensured that, even if the hands or gloves are wet, the water on the hands or the gloves in contact with the water absorbing member will move towards the water absorbing member and be absorbed thereby. This prevents a water film from existing between the hands or the gloves and the water absorbing member, so that a sufficient coefficient of friction exists therebetween to enable the packing bag to be ripped or torn open with sufficient tearing force. The present packing bag construction is particularly well suited for holding orthopedic casting materials and the like which must remain in a sealed closure until use and which are typically handled using hands or gloves which may be wet and slippery. In addition, the water absorbing member according to the present invention can be mounted on the surface of the packing bag by use of a simple construction such as by adhesion, so that the manufacturing steps for said packing bag are simple and easy and no complicated manufacturing apparatus is needed.

6 Claims, 5 Drawing Sheets

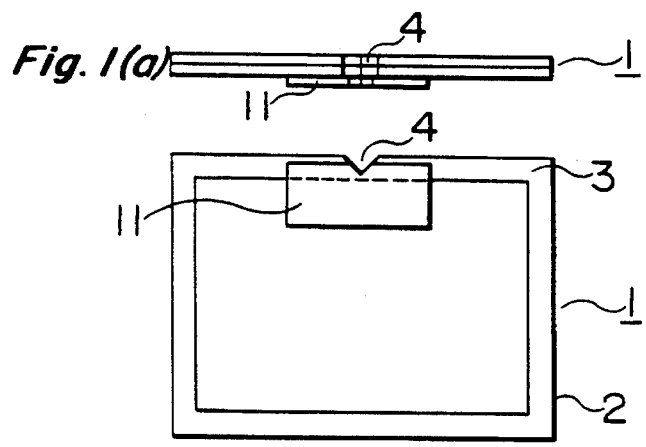
Fig. 1(a)
Fig. 1(b)
Fig. 1(c)
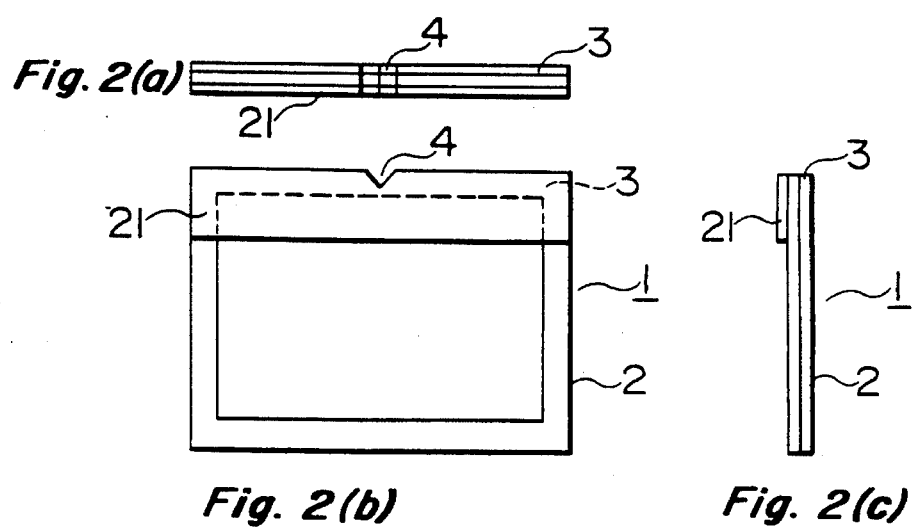
Fig. 2(a)
Fig. 2(b)
Fig. 2(c)
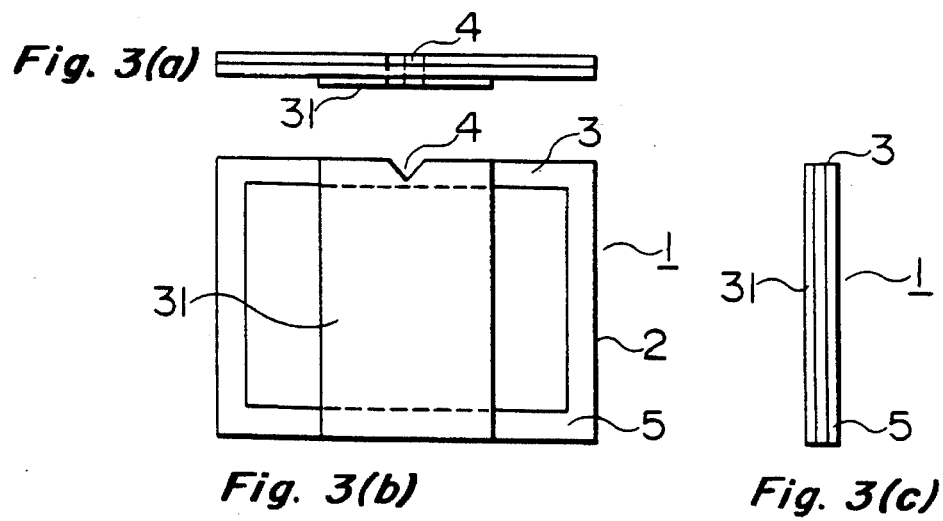
Fig. 3(a)
Fig. 3(b)
Fig. 3(c)

Fig. 7(a)
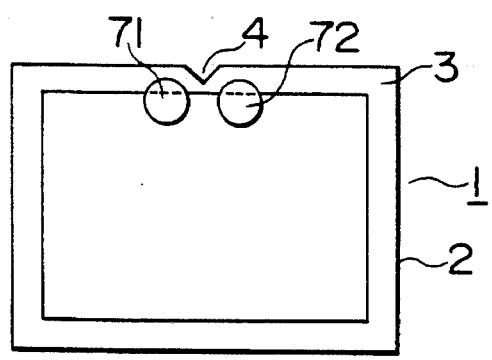
Fig. 7(b)
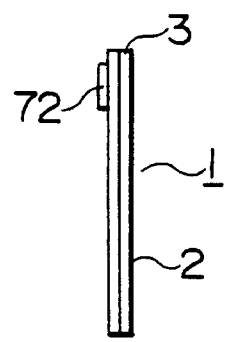
Fig. 7(c)
Fig. 8(a)   Fig. 8(b)   Fig. 8(c)
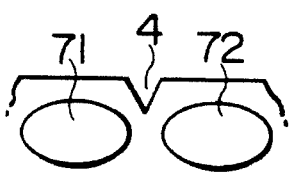  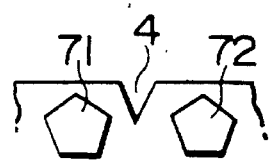
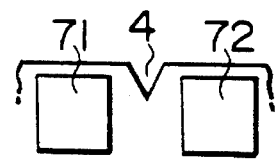 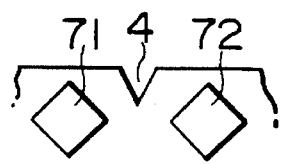
Fig. 8(d)   Fig. 8(e)
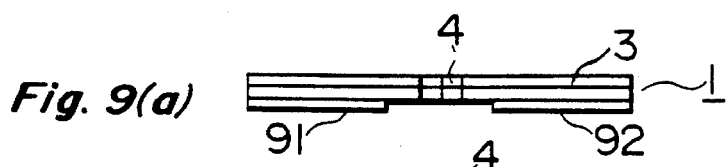
Fig. 9(a)
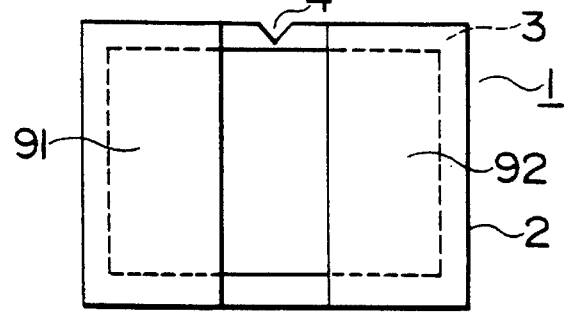
Fig. 9(b)
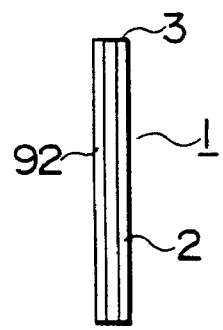
Fig. 9(c)

PACKING BAG

Applicants hereby claim foreign priority benefits under 35 USC §119 of corresponding Japanese patent application Ser. No. (Hei) 4-18909, filed Feb. 28, 1992.

BACKGROUND OF THE INVENTION

1. Field of the Invention

The present invention relates to packing bags comprising overlaying films sealed together along the peripheral or circumferential portions of the films, and more particularly, to an improved seal-breaking structure for such packing bags.

2. Description of the Prior Art

Packing bags made by laying films one upon the other and sealing the peripheral or circumferential edge portions of the films are used in various fields. In order to access and utilize the contents of such packing bags, the packing bag must be opened by breaking the seal. A cutting tool or instrument such as scissors can be used for opening the packing bag, but it is desirable for convenience and utility to be able to tear open such packing bags by hand.

In the medical field, a commonly used orthopedic cast material is a water-curable cast material made by applying polyurethane polymer resin to a base fabric. This cast material hardens upon contact with the moisture present in the air and must therefore be held in a tightly sealed container such as in a film packing bag to avoid premature hardening. This cast material can furthermore contain a water-soluable tack-free agent such as a surface-active agent, ester of fatty acid, or the like which agent prevents the resin component of the cast material from adhering or sticking to the hands of a person, such as a physician or an orthopedic or cast technician, as the cast material is applied or wound around an injured or otherwise affected or diseased body part such as a limb or the like. However, a perfectly tack-free cast material cannot be realized, so that the cast technician or other applicator will wear gloves for the procedure in many cases. When such a cast material is placed or mounted onto an affected or a diseased body part, the cast material is taken out of the bag and is dipped into water, and is then wound around or otherwise applied to the diseased body part. As the cast material is handled using the thus wetted gloves, some of the tack-free agent and water will be present on the surface of the gloves. When the cast technician tries to open subsequent packing bags, the gloves will be quite slippery due to the water and the tack-free agent thereon making grasping and tearing open subsequent bags quite difficult. Numerous attempts have been made to provide a solution to this problem, for instance, reducing the thickness of the film used to make the packing bag so as to make the packing bag easier to tear. Another proposed solution is to use a material with a directional tear characteristic. Still another proposed solution is to increase the depth of the notch provided to facilitate the tearing of the packing bag. However, sufficiently satisfactory packing bags could not be obtained using such means without the undesirable result of lowering its durability.

Another alternative to facilitate the opening and seal breaking of such packing bags has been proposed by the present applicants wherein the bag structure is made in such a manner that, in at least one sealed peripheral or circumferential side of the packing bag, there is provided a notch, and also two or more holes extending through the bag adjacent two opposite sides of the notch. A user's fingers can be inserted and hooked in the holes to enable the user to grasp and tear open the packing bag, even when wearing wet gloves. One shortcoming of this alternative is the disposal of the tailings produced when the through holes are made in the bag. Another shortcoming is that the required manufacturing apparatus for the bag can be large and complicated. In addition, even to provide through holes of a size just sufficient for the finger to be inserted, it is necessary to make the width of the sealed peripheral portion more than 20 mm, resulting in lack of uniformity of sealing strength.

Another possible application for the present invention is in the field of packaging for foods, wherein various film packing bags made in such a manner that foodstuffs can be enclosed and sealed therein and be directly heated therein such as by boiling. This type of packing bag is also often handled by wet hands during food preparation and cooking. Furthermore, the packing bags themselves when removed from the boiling water after heating are also wet, and therefore difficult to open with hands which are wet and slippery so as to have a drawback similar to the shortcomings discussed above.

SUMMARY OF THE INVENTION

The present packing bag construction overcomes many of the above discussed disadvantages and shortcomings associated with the known prior art packing bag constructions and teaches the construction and operation of an improved packing bag providing water absorbing means or members located on at least a portion of the outer surface thereof adjacent one or more sealed peripheral or circumferential portions of the bag. The packing bag according to the present invention can also include optional seal breaking means, for instance, a seal breaking portion such as a notch formed in at least one side or edge portion of the sealed periphery or circumference of the packing bag, the water absorbing member being located adjacent the seal breaking portion. The water absorbing member according to the present invention can include water absorbing materials having the property of absorbing thereinto any water located on the surface thereof, and also materials having a surface state which expels water when contacted with a glove.

OPERATION OF THE INVENTION

The present packing bag construction is opened by grasping the packing bag with gloved or ungloved hands or fingers contacting the water absorbing member or members. All or most of any water, tack-free agent, or the like located on the surface of the glove or hand and in contact with the water absorbing member will be drawn towards the water absorbing member so as to be absorbed thereby. This prevents a slippery water or other film layer from existing between the water absorbing member and the surface of the fingers of the hand or glove in contact therewith, so that the packing bag can be torn open without slipping or a hydroplaning phenomenon between the fingers or gloves and the water absorbing member.

It is therefore an object of the present invention to enable opening a bag with wet and slippery hands or gloves.

Another object is to provide one or more no-slip surfaces on the outside of a packing bag to enable grasping and tearing open the packing bag with wet hands or gloves.

Another object is to provide one or more surfaces on the outside of a bag to absorb water and other slippery agents present on the hands to enable grasping and tearing open the bag.

Another object is to provide a packing bag for items such as orthopedic cast materials and the like which is easy to open.

Another object is to provide a sealed packing bag for orthopedic cast materials and the like which can be quickly and easily opened without scissors or other tools.

Another object is to provide a film packing bag which is easy to manufacture and easily opened by tearing, even with wet and slippery hands.

BRIEF DESCRIPTION OF THE DRAWINGS

FIGS. 1(a), 1(b), and 1(c) through FIGS. 7(a), 7(b), and 7(c) show top views, front views, and side views, respectively, of several different embodiments of a packing bag constructed according to the teachings of the present invention.

FIGS. 8(a) through 8(e) illustrate various alternative shapes for the water absorbing members shown in FIGS. 7(a) through 7(c).

FIGS. 9(a), 9(b), and 9(c) through FIGS. 11(a), 11(b), and 11(c) show top views, front views, and side views, respectively, of still other embodiments of a packing bag constructed according to the teachings of the present invention.

DESCRIPTION OF THE PREFERRED EMBODIMENTS

Figure 4A:

Embodiments of the present invention will now be described by reference to the drawings.

Referring to the drawings more particularly by reference numbers wherein like numerals refer to like parts, FIGS. 1(a), 1(b) and 1(c) show one embodiment of a packing bag, designated by the numeral 1, formed of films laid one upon the other and sealed along the peripheral or circumferential portions 2 thereof. In one (sealed) side portion 3 of the thus sealed periphery or circumference, a notch 4 is provided as a seal breaking means. On a portion of the outer surface of the bag 1 adjacent the notch 4, there is provided a water absorbing member 11 having a rectangular shape.

FIGS. 2(a), 2(b) and 2(c) show another embodiment of the present invention constructed in such a manner that a water absorbing member 21 is provided along the sealed side portion 3 adjacent the notch 4.

FIGS. 3(a), 3(b) and 3(c) show another embodiment of the present invention constructed in such a manner that a water absorbing member 31 is provided extending from the sealed side portion 3 adjacent the notch 4, to a sealed side portion 5 opposed thereto.

Figure 4B:
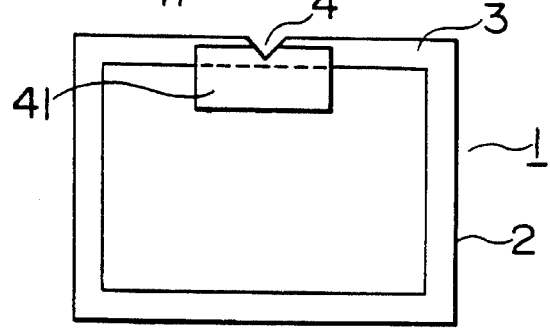
Figure 4C:
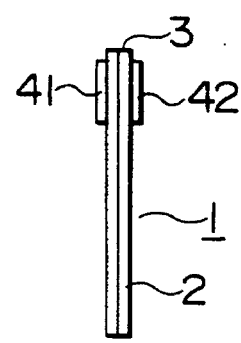

FIGS. 4(a), 4(b) and 4(c) show another embodiment of the present invention constructed in such a manner that water absorbing members 41 and 42, each having the same shape as the water absorbing member 11 shown in FIG. 1, are provided on respective opposite surfaces of the packing bag 1.

Figure 5A:
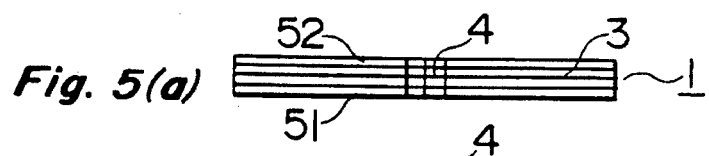
Figure 5B:
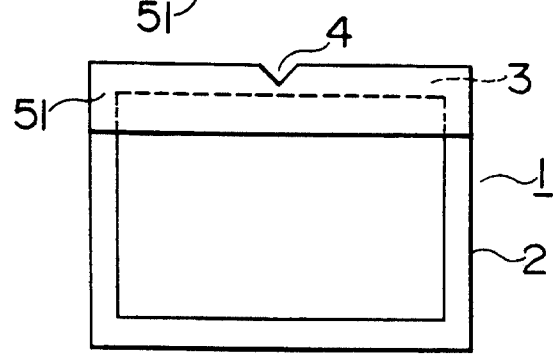
Figure 5C:
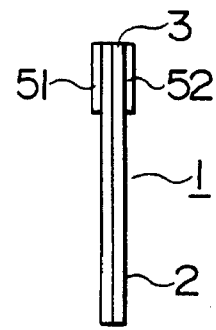

FIGS. 5(a), 5(b) and 5(c) show still another embodiment of the present invention constructed in such a manner that water absorbing members 51 and 52, each having the same shape as the water absorbing member 21 shown in FIG. 2, are provided on the respective opposite surfaces of the packing bag 1.

Figure 6A:
Figure 6B:
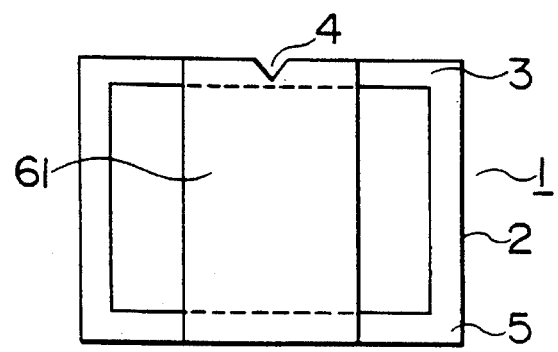
Figure 6C:
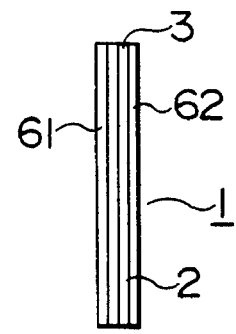

FIGS. 6(a), 6(b) and 6(c) show still another embodiment of the present invention constructed in such a manner that water absorbing members 61 and 62, each having the same shape as the water absorbing member 31 shown in FIG. 3, are provided on the respective opposite surfaces of the packing bag 1.

FIGS. 7(a), 7(b) and 7(c) show still another embodiment of the present invention constructed in such a manner that water absorbing members 71 and 72, each having a round shape, are provided adjacent both sides of the notch 4 provided in the sealed side portion 3 of the packing bag 1.

FIGS. 8(a) through 8(e) show various alternative shapes for the water absorbing members 71 and 72 shown in FIG. 7, of which FIG. 8(a) shows oval shaped water absorbing members, FIG. 8(b) shows star-shaped water absorbing members, FIG. 8(c) shows pentagonal water absorbing members, FIG. 8(d) shows square water absorbing members, and FIG. 8(e) shows rhombic water absorbing members.

FIGS. 9(a), 9(b) and 9(c) show still another embodiment of the present invention constructed in such a manner that water absorbing members 91 and 92 are provided adjacent respective opposite sides of the notch 4 in the sealed side portion 3, extending from the sealed side portion 3 to the seal side portion 5 opposed thereto. Further, the water absorbing members of the embodiments of FIGS. 7 through 9 can be provided on only one surface of the packing bag 1, as shown, and alternatively, on both surfaces thereof.

Figure 10A:
Figure 10B:
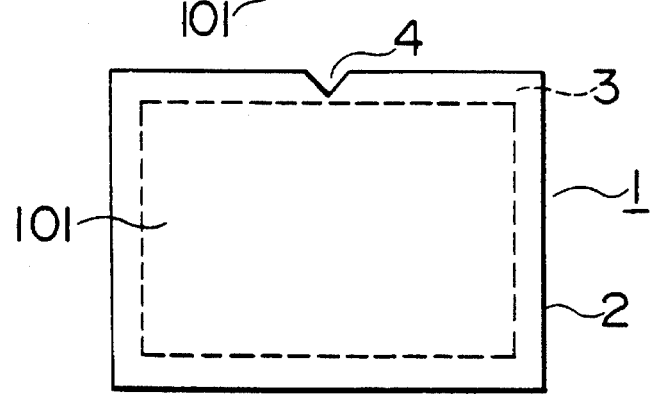
Figure 10C:
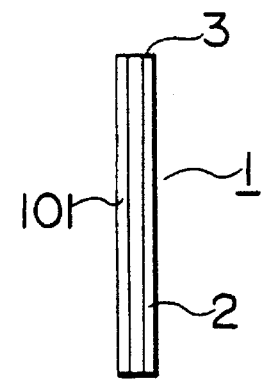

FIGS. 10(a), 10(b) and 10(c) show still another embodiment of the present invention constructed in such a manner that a water absorbing member 101 is provided covering the whole of the outer surface of the packing bag 1. In this case, such whole-surface-covering water absorbing member 101 can be provided on only one surface of the packing bag as shown, and alternatively, on both surfaces.

Figure 11A:
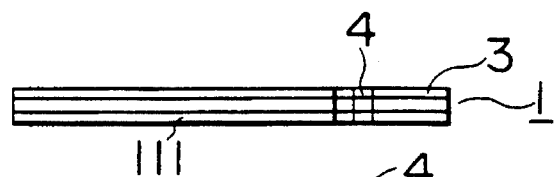
Figure 11B:
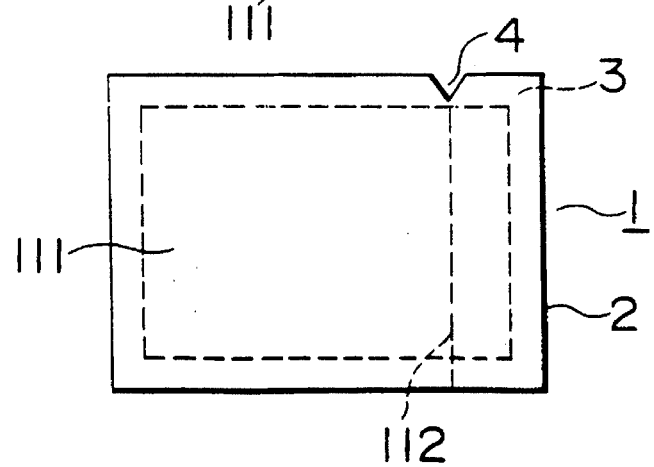
Figure 11C:
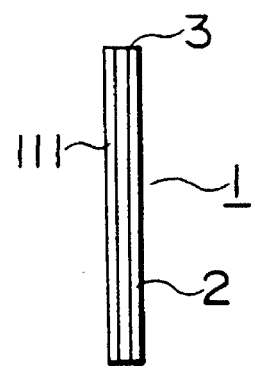

FIGS. 11(a), 11(b) and 11(c) show still another embodiment of the present invention constructed in such a manner that a water absorbing member 111 is provided covering the whole of the outer surface of the packing bag 1 as in the case of FIG. 10 and further including a slit 112 in the water absorbing member 111 extending from the notch 4 in the sealed side portion 3, to the opposite end of the bag so as to reduce the required tearing force for opening the bag.

It should be noted that in all the foregoing embodiments, like notches are provided in the sealed side portions of the respective packing bags, but the provision of such notches is not always necessary.

As the film material of the packing bag, any suitable material providing desirable characteristics for a particular application can be used. For instance, multi-layer films made of: polyester/aluminum/polyethylene/linear low density polyethylene; K nylon/aluminum/polypropylene; polyethylene/polyvinylidene chloride/polyethylene; polyethylene/K nylon/polyethylene; and so forth can be used. Desirable characteristics which can be considered when selecting film material include the tear characteristics of the material.

As the materials used for the water absorbing member, any suitable material having the desired water absorbing characteristics can be used such as, for instance, paper, nonwoven fabric, cloth, foamed material, and so forth. More particularly, as for paper materials, those papers which are made in such a manner that a vegetable fiber, an animal fiber, or a synthetic fiber, and so forth are intertwined and glued together; papers made in the Western way such as rolls of newspaper print, printing paper, writing paper, drawing paper, packing paper, thin paper, and so forth; paperboards such as corrugated cardboard, white paperboard, straw board, chipboard, color board; and Japanese papers such as (sliding) screen paper (Japanese SHOJI paper), calligraphic paper, tissue paper, paper cotton, and so forth, can be used. The thickness of the water absorbing member can be from about 0.01 to about 5 mm, and is preferably from about 0.04 to about 1 mm thick. So-called sand paper composed by bonding to the surface of the paper, small particles of an inorganic substance such as a metal powder, a mineral powder or the like can also be used. However, the use of such a paper as has a surface treated with a hydrophobic resin to thereby coat the fiber surface or the inter-fiber portions of the paper therewith is not undesirable.

As the nonwoven fabric alternative for the water absorbing member, those fabrics which are manufactured in accordance with the dry type system, or with the wet type system, by use of materials such as rayon, vinylon, polyvinylidene chloride, polyester, polyamide, acetate polypropylene, and so forth, and having such a wide range of weight per unit area as from about 5 to about 300 g/m$^2$, can be used.

Preferably, a material such as rayon which has a high water absorbing characteristic, a weight per unit area of about 15 to about 100 g/m$^2$, a thickness of about 0.01 to about 5.0 mm, and a low tear strength is used.

As the cloth alternative for the water absorbing member, a woven cloth or a knitted cloth such as, for instance, gauze, shirting, broad cloth, lace, and so forth, which comprises natural fiber, semi-synthetic fiber, synthetic fiber or the like, can be used. Preferably a cloth is used which can be easily ripped up by hand at least longitudinally or laterally. To this end, ordinarily a method of reducing the thickness of the yarns is used.

The foamed sheets which can be used for the water absorbing member can be broadly divided into two kinds, open-cell foamed sheets, and closed-cell foamed sheets. The materials of the foamed sheets can include polyvinyl alcohol, polyvinyl formal, polyurethane, ethylene-vinyl acetate copolymer, natural rubber, polyvinyl chloride, and polymers containing water absorbing high-polymer molecules. Those materials which are open-cell foamed materials having a hydrophilic nature, a small cell diameter and a high expansion ratio are preferable.

TABLE 1

| Structure | | | Water absorbing characteristic | | | |
|---|---|---|---|---|---|---|
| | | | High | Middle Material (Official Regain) | Low | None |
| | | | Rayon (11.0) Cuprammonium rayon (11.0) Acetyl cellulose (6.5) Vinylon (5.0) Cotton (8.5) Wool (15.0) Silk (11.0) Flax (12.0) Paper Polyvinyl formal Rubber or plastics containing water-absorbing polygon | Polyamide (4.5) Polyacrylonitrile (2.0) Polycrahl (3.0) Ethylene vinyl acetate copolymer | Polyester (0.4) Poly- ethylene (1.0) | Polyethylene Polypropyrene Polyvinyl chloride Polyvinyliden chloride Fluorine fiber |
| Fiber assemblage | | | | | | |
| Density | High ↑ ↓ Low | Density like that of paper | ○ | ○ | ○ | Δ |
| | | Density like that of nonwover fibric | ○ | ○ | ○ | Δ |
| | | Density like that of woven cloth | ○ | ○ | Δ | X |
| | | Density like that of meshes of a net | ○ | ○ | Δ | X |
| Foamed body | | | | | | |
| Open-cell foamed bodies | | | | | | |
| Density | High ↑ ↓ Low | Foamed sheets which are small in cell diameter and high in the expansion ratio | ○ | ○ | ○ | Δ |
| | | Foamed sheets which are small in cell diameter and intermediate in the expansion ratio | ○ | ○ | ○ | X |
| | | Foamed sheets which are large in cell diameter and low in the expansion ratio | ○ | ○ | Δ | X |
| Closed-cell foamed bodies | | | | | | |

TABLE 1-continued

| Density | | | | | | |
|---|---|---|---|---|---|---|
| High ↑ | Foamed sheets which are small in cell diameter and high in the expansion ratio | ○ | △ | | X | X |
| | Foamed sheets which are intermediate in cell diameter and intermediate in the expansion ratio | ○ | | ○ | X | X |
| ↓ Low | Foamed sheets which are large in cell diameter and low in the expansion ratio | ○ | ○ | | X | X |

Table 1 shows the contents of application of the present invention arranged in view of the material and structure. Along the axis of the abscissa, the water absorbing characteristics of the materials are plotted, with the water absorbing function being progressively higher towards the left-hand side and lower towards the right-hand side of the axis of the abscissa. On the axis of the ordinate, fiber assemblages, that is, paper, nonwoven fabric and cloth, are arranged with the higher density materials towards the top, whereas the foamed bodies are divided into open-cell foamed bodies and closed-cell foamed bodies, which are further divided in accordance with the combination of the cell diameter and the expansion ratio, as shown. In Table 1, the mark "○" stands for good materials having or exhibiting no slip at all, the mark "△" stands for usable materials, and the mark "X" stands for unusable materials. From Table 1, it may be understood that those materials which are higher or better in water absorbing characteristic are most desirable. As to structure, the fiber assemblages are better if they are higher in density, and, as for the foamed bodies, open-cell foamed bodies which have smaller cell diameters and larger expansion ratios are more preferable. However, it should be noted that those materials which are high in water absorbing properties are all usable without regard to the types of structure. Further, even in the case of a material having a low water absorbing characteristic, such material can be made usable by making its density higher in respect of the structure, whereby the portions between the fibers or the cell walls of the foamed bodies will absorb the water by capillarity. Of the materials shown in said Table 1, even those which are low in water absorption can exhibit an excellent effect if they are blended with hydrophilic materials. For instance, such hydrophilic materials can include materials having groups such as —OH, —$CONH_2$, —COOH, —$NH_2$, —$COO^-$, —$SO_3^-$, —$NR_3^+$, or the like, and such as those hydrophilic groups whose chain high molecules have no cross linkage. In addition, materials having low water absorption can be blended with starches, cellulosic tannins, lignins, polysaccharides, polyvinyl alcohols (PVAs), polyethylene oxides, acrylic acids, maleic anhydrides, phthalic acids, polyesters, polyoxy compounds, acrylamides, polyvinyl pyrrolidones and copolymers thereof. Materials treated with a surface-active agent are particularly preferable.

Further, an important characteristic for the water absorbing member is to have a good manual tearability, or ability to be easily torn by hand. For instance, the water absorbing member should desirably have a manual tearability of about 5 kg or less and, preferably about 0.2 kg or less, as measured and proved using the testing method for tear resistance of a film set forth in Japanese Industrial Standard JIS K6772.

The methods of manufacturing packing bags according to the present invention can be broadly divided into three methods. In the first method, after the bag is formed, the water absorbing member is mounted or attached thereto. In the second method the water absorbing member is attached to the bag while the bag is being manufactured. In the third method, the water absorbing member is joined to the material or films before the films are manufactured into the bag. The first method utilizes a water absorbing member having an adhesive or a bonding agent applied to one surface thereof for attachment to the film. In this case, the water absorbing member having an adhesive or a bonding agent applied thereto can be cut to a suitable size and adhered or affixed to the surface of the bag by hand. Alternatively, a long strip of water absorbing material to which an adhesive or a bonding agent has been applied, can be adhered, by use of a labelling machine, to bags which are made to continuously flow on a conveyor. This method is possible even though the material is manufactured in small lots, and the facility investment required is relatively small, which is an advantage. The second method is carried out in such a manner that a sticking mechanism is provided between the film material delivery portion of a bag making machine and a sealing step, or between the sealing step and a cutting step, so that, simultaneously when each bag is made, a water absorbing member with an adhesive or a bonding agent is joined to the bag. The third method is performed in such a manner that an adhesive or a bonding agent is applied to one surface of the film material, and a water absorbing member is attached and pressure-bonded to the bonding agent.

Figure 12:
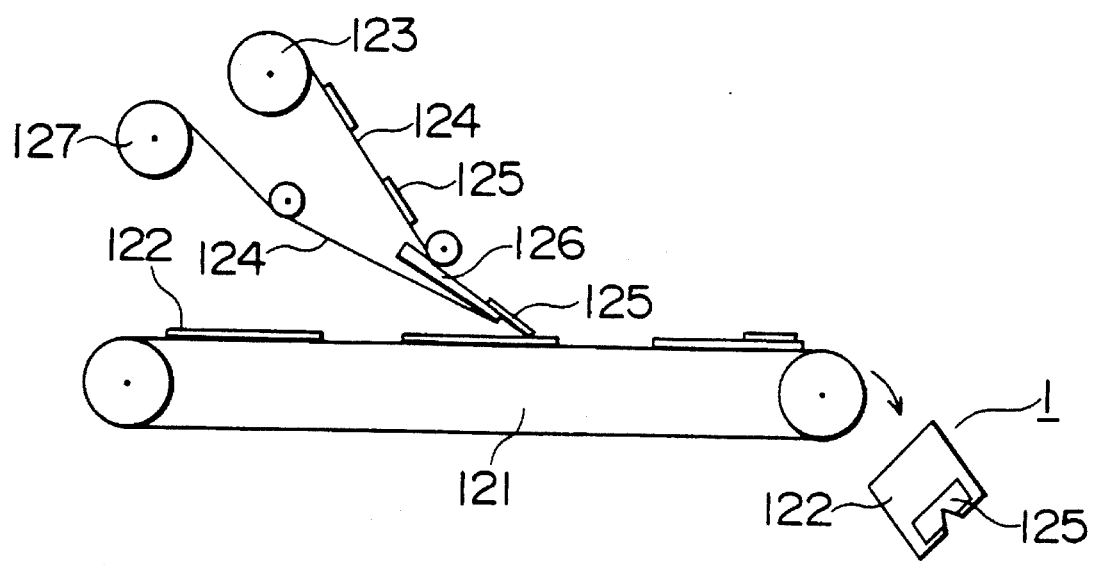
FIG. 12 is a schematic diagram illustrating an apparatus and a method for the manufacture of a packing bag according to the present invention.

FIG. 12 is a schematic diagram explaining the first method for manufacturing packing bags according to the present invention, in which numeral 121 denotes a conveyor. From the left-hand side, packing bags 122 are made to successively flow toward the right side on the conveyor. From a roll 123, water absorbing members 125, each provided with an adhesive and placed on a mount or mounting paper 124, are led to the conveyor 121, and then the water absorbing members 125 are each peeled off from the mounting paper 124 by a peeling mechanism 126 and adhered to a predetermined portion of the surface of a packing bag 122, while the mounting paper 124 is taken up onto a roll 127. As a result, from the right or terminal end of the conveyor 121, the packing bags 1 each having the water absorbing member attached thereto are produced.

Figure 13:
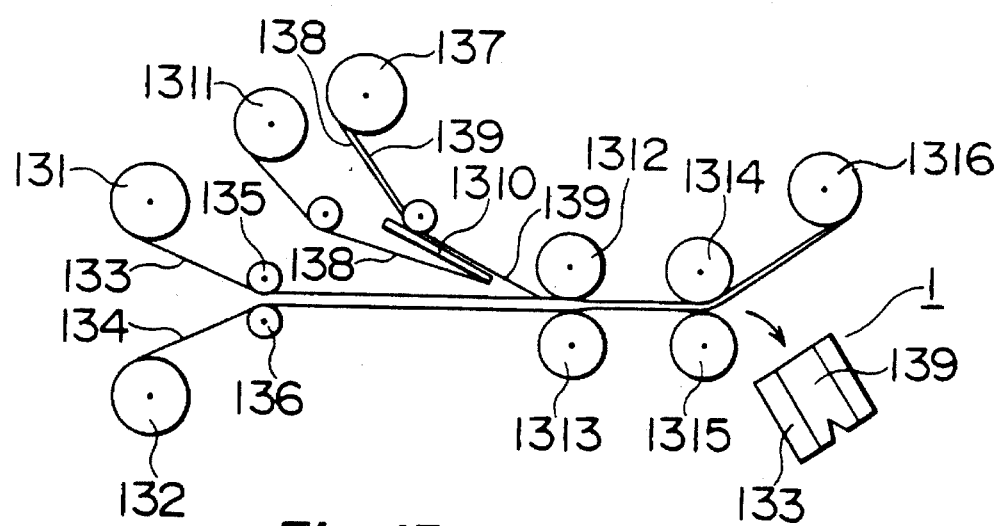
FIG. 13 is a schematic diagram illustrating an apparatus and a method for the manufacture of a packing bag according to the present invention.

FIG. 13 is a schematic diagram explaining the second method wherein material films 133 and 134 delivered from rolls 131 and 132, respectively, are laid one upon the other by means of guide rolls 135 and 136, a water absorbing member 139 with an adhesive placed on a mounting paper 138 delivered from a roll 137 is guided onto the upper material film 133, and the water absorbing member 139 peeled off from the mounting paper 138 by a peeling mechanism 1310 is adhered onto the material film 133, while the mounting paper 138 is taken up onto a roll 1311. The two material films 133 and 134 are sealed by sealing rolls 1312 and 1313 and cut into a final packing bag shape by die-cutting rolls 1314 and 1315, while the cut portions of the film materials 133 and 134 are taken up onto a roll 1316. In this way, packing bags 1, each having a water absorbing member affixed thereto, are produced.

The function or operation and advantages of the water absorbing member constructed in accordance with the present invention will now be explained. The water or the surface-active agent present on the surface of the gloves handling the packing bag is in a free state and is in the form of droplets or a water film layer. If the material films comprising the packing bag are non-water absorbing, are flat and smooth, or even have a surface texture such as projections and depressions comprising gently curved surfaces, when pinched by the gloves, the water droplets or water film will be squeezed to form a very thin water film between the surfaces of the material film and the surfaces of the gloves. This water film substantially reduces the friction between the gloves and the material films, as a result of which the gloves become very slippery, so that it is difficult to tear open the packing bag. Furthermore, even grasping the material films more firmly results only in a further thinning, but not removal, of the water films, and therefore, the slipping problem remains. Still further, even when using material films which are embossed or otherwise formed so as to have a surface with a pattern of projections and depressions thereon such as by use of a metal sealing mold provided with projections and depressions, the gloves are very soft and will conform to the projections and depressions on the surface of the material films, as a result of which the water films still remain. According to the present invention, the one or more water absorbing members provided on the surfaces of the packing bag absorb the water droplets and the surface-active agent, so that no significant water films are formed between the gloves and the material films. More particularly, the amount of the water forming the water films on the surfaces of the gloves, or the amount of the surface-active agent thereon is very small, for instance only about several ml, and thus, by provision of the water absorbing member or members on the surfaces of the material films, the water films can be easily removed. Moreover, even in a case where a bag with its water absorbing member saturated with water or the surface-active agent is gripped by gloves, the extra water or surface-active agent will still be squeezed out between the gloves and the packing bag, so that no water film is present.

The packing bag according to the present invention can be applied as a packing bag which is required to have airtightness and enclose therein a thing required to be shut off from the outside world but must be opened when said thing is to be used. The packing bag according to the present invention is particularly suited as a packing bag which must be handled by wet hands.

Thus there has been shown and described a novel packing bag construction which fulfills all the objects and advantages set forth above. It will be apparent to those skilled in the art, however, that many changes, modifications, variations and other uses and applications for the subject invention are possible. All such changes, modifications, variations and other uses and applications which do not depart from the spirit and scope of the invention are deemed to be covered by the invention, which is limited only the claims which follow.

What is claimed is:

1. In a packing bag for orthopedic casting material formed of a film material, said packing bag having at least one outer surface located adjacent to a peripheral portion of the packing bag, the peripheral portion of the packing bag comprising overlaying film layers joined together to form a sealed closure therebetween, the improvement comprising a water absorbing paper member located on at least one outer surface of said packing bag adjacent said peripheral portion thereof, said water absorbing paper member having a manual tearability of no more than about 5 kgs and said water absorbing member having one surface bonded to said outer surface of said packing bag and an opposite surface having particles of an inorganic substance located thereon.

2. The packing bag according to claim 1 wherein said peripheral portion further comprises a notch formed in said overlaying film layers.

3. In a packing bag for orthopedic casting material having an outer surface adjacent to at least one sealed peripheral portion characterized by film material portions laid one upon the other and sealed together, the improvement comprising the sealed peripheral portion having seal breaking means at least one location thereon, and water absorbing paper members on said outer surface adjacent opposite sides of said seal breaking means.

4. The packing bag according to claim 3 wherein said seal breaking means comprise a notch formed in the film material portions.

5. The packing bag according to claim 4 wherein at least one of said water absorbing paper members includes a slit formed therein adjacent said notch.

6. A packing bag comprising films laid one upon the other and sealed together along at least a portion of the peripheral portions thereof, each of said films having an outer surface located adjacent to the sealed portion of the peripheral portions thereof, the sealed portion having a notch formed therein, and water absorbing paper members provided on at least one of said outer surfaces adjacent opposite sides of said notch.

* * * * *